United States Patent [19]

Suciu et al.

[11] Patent Number: 5,382,701
[45] Date of Patent: Jan. 17, 1995

[54] USE AS CATALYST IN THE HYDROFORMYLATION OF OLEFINIC FEEDSTOCK TO HIGHER ALDEHYDES AND HIGHER ALCOHOLS

[75] Inventors: Elena N. Suciu, Bridgewood; Joel R. Livingston, Jr., Basking Ridge; Edmund J. Mozeleski, Califon, all of N.J.

[73] Assignee: Exxon Chemical Patents Inc., Linden, N.J.

[21] Appl. No.: 154,657

[22] Filed: Nov. 18, 1993

Related U.S. Application Data

[62] Division of Ser. No. 6,910, Jan. 21, 1993.

[51] Int. Cl.$^6$ .............................................. C07C 45/50
[52] U.S. Cl. ...................... 568/454; 558/78; 568/429; 568/451
[58] Field of Search .................. 558/78; 568/454, 451, 568/429, 426

[56] References Cited

U.S. PATENT DOCUMENTS

| | | | |
|---|---|---|---|
| 4,399,312 | 8/1983 | Russell et al. | 568/454 |
| 4,625,067 | 11/1986 | Hanin | 568/451 |
| 4,625,068 | 11/1986 | Young | 568/454 |
| 4,642,388 | 2/1987 | Young | 568/454 |
| 4,731,486 | 3/1988 | Abatjoglou et al. | 568/454 |
| 4,808,757 | 2/1989 | Cornils et al. | 568/454 |
| 5,059,710 | 10/1991 | Abatjoglou et al. | 558/78 |
| 5,180,854 | 1/1993 | Abatjoglou et al. | 568/454 |
| 5,223,648 | 6/1993 | Herrmann et al. | 568/454 |
| 5,233,093 | 8/1993 | Pitchai et al. | 568/454 |

FOREIGN PATENT DOCUMENTS

| | | | |
|---|---|---|---|
| 8700881 | 11/1988 | Netherlands | B01D 13/00 |
| 2085874 | 5/1982 | United Kingdom | C07C 45/50 |

OTHER PUBLICATIONS

Ahrland et al., "The Relative Affinites of Coordinating Atoms for Silver Ion, Part II Nitrogen, Phosphorus and Arsenic", Chemical Society, 1958, pp. 276–288.

Imyanitov et al., All–Union Scientific Research Institute of Petrochemical Processes, Neftekhimiya, 32, No. 3:200–7 (May–Jun. 1992).

Gosser et al., Reverse Osmosis in Homogeneous Catalysts, Journal of Molecular Catalysis, 2(1977), pp. 253–263.

Primary Examiner—Werren B. Lone
Attorney, Agent, or Firm—J. J. Mahon

[57] ABSTRACT

A method for producing a potassium paradiphenyl phosphino sulfonate ligand which comprises reacting potassium diphenyl phosphide with a lithium salt of para-chloro benzenesulfonic acid in the presence of tetrahydrofuran at elevated temperatures.

11 Claims, No Drawings

USE AS CATALYST IN THE HYDROFORMYLATION OF OLEFINIC FEEDSTOCK TO HIGHER ALDEHYDES AND HIGHER ALCOHOLS

This is a division of application Ser. No. 006,910, filed Jan. 21, 1993.

The present invention relates generally to a novel ligand that is useful for hydroformylation of higher α-olefins in an aqueous emulsion. The ligand is a potassium para-diphenyl phosphino benzene sulfonate which is synthesized rapidly and in extremely high yields.

BACKGROUND OF THE INVENTION

Hydroformylation reactions involve the preparation of oxygenated organic compounds by the reaction of carbon monoxide and hydrogen (i.e., synthesis gas) with carbon compounds containing olefinic unsaturation. The reaction is typically performed in the presence of a carbonylation catalyst and results in the formation of compounds, for example, aldehydes, which have one or more carbon atoms in their molecular structure than the starting olefinic feedstock. By way of example, higher alcohols may be produced by hydroformylation of commercial $C_6$-$C_{12}$ olefin fractions to an aldehyde-containing oxonation product, which on hydrogenation yields the corresponding $C_7$-$C_{13}$ saturated alcohols. The crude product of the hydroformylation reaction will contain catalyst, aldehydes, alcohols, unreacted olefin feed, synthesis gas and by-products.

A variety of transition metals catalyze the hydroformylation reaction, but only cobalt and rhodium carbonyl complexes are used in commercial plants. The reaction is highly exothermic, i.e., the heat release is approximately ca 125 kJ/mol (30 kcal/mol). The position of the formyl group in the aldehyde product depends upon the olefin type, the catalyst, the solvent, and the reaction conditions. Reaction conditions have some effect and, with an unmodified cobalt catalyst, the yield of straight chain product from a linear olefin is favored by higher carbon monoxide partial pressure. In the hydroformylation of terminal olefinic hydrocarbons, the use of a catalyst containing selected complexing ligands, e.g., tertiary phosphines, results in the predominant formation of the normal isomer.

In commercial operation, the aldehyde product is typically used as an intermediate which is converted hydrogenation to an alcohol or by aldolization and hydrogenation to a higher alcohol. The aldol-hydrogenation route is used primarily for the manufacture of 2-ethylhexanol from propylene that is converted to n-butyraldehyde.

Much research in the past 25 years has been directed to improving reaction selectivity to the linear product. Introduction of an organophospnine ligand to form a complex, e.g., $Co(CO)_6[P(n-C_4H_9)_3]_2$, significantly improves the selectivity to the straight chain alcohol.

Recent developments of low pressure rhodium catalyst systems have been the subject of a considerable body of patent art and literature, and rhodium-triphenyl phosphine systems have been widely, and successfully, used commercially for the hydroformylation of propylene feedstocks to produce butyraldehyde.

Homogeneous catalysts formed from ligated metal atoms can perform very selective chemistries with high turnover rates. For example, rhodium complexes containing phosphine ligands have ideal properties as catalysts in the hydroformylation process used in making long chain aldehydes because of their propensity to form the linear rather than branched isomers. The linear aldehydes which can be formed with rhodium catalyst complexes are needed for formulating biodegradable detergents, plasticizers, specialty polymers, etc. Homogeneous rhodium catalyst complexes have a unique role in this chemistry in that they can take a linear terminal olefin and convert it into a predominantly linear aldehyde.

A typical homogeneous rhodium complex catalyst is formed with triphenylphosphine ligands in the presence of carbon monoxide and hydrogen. The rhodium bonds to the triphenylphosphine ligand through a phosphorous atom. A large number of complexes are formed between rhodium, triphenylphosphine, hydrogen, and carbon monoxide, because they form loosely bound molecular species which are involved in multiple equilibria as they dissociate and recombine with ligands in solution. One of the complexes can be a very active catalyst for the hydroformylation reaction which converts linear olefins into the next higher carbon number linear aldehydes by the addition of carbon monoxide and hydrogen. In addition, the catalyst converts some of the product aldehyde to dimer and trimer condensation products. The isomerization activity of the catalyst in extremely undesirable in applications designed to produce long chain linear aldehydes. Linear aldehydes containing between 12 to 15 carbon are readily hydrogenated to linear alcohols which are premium products for formulating biodegradable liquid detergents.

Others have synthesized high molecular weight phosphine ligands for use as homogeneous catalysts. High molecular weight polymeric phosphine ligands are synthesized by reacting polyvinylchloride, polychloroprene or brominated polystyrene with lithium diphenylphosphide at 20° C. to 25° C. These homogeneous catalysts containing bulky ligands are thought to be more easily separated from the reaction products by ultrafiltration. See Imyanitov et al., All-Union Scientific Research Institute of Petrochemical Processes, *Neftekhimiya*, 32, No. 3:200-7 (May–June 1992).

One conventional rhodium ligand used in the hydroformylation of higher α-olefins, such as 1-dodecene in an aqueous emulsion catalytic process, is sodium p-diphenyl phosphino benzoate, i.e., $Ph_2P(pC_6H_4COO_3Na)$. As discussed in Great Britain Patent Application No. 2,085,874, filed on Aug. 21, 1981, this rhodium ligand complex is active at low temperature and pressure, and gives a high selectivity to the normal isomer.

Still others have synthesized a rhodium ligand complex using a $Ph_2P(m-C_6H_4SO_3Na)$ ligand as shown in Ahrland et al., "The relative Affinities of Co-ordinating Atoms for Silver Ion. Part II.[1] Nitrogen, Phosphorus, and Arsenic.[2] *Chemical Society*, 1958, pp. 276-288. The $Ph_2P(m-C_6H_4SO_3Na)$ ligand was synthesized by slowly adding 10 grams of triphenylphosphine, with cooling, to a mixture of 20% $SO_3$-$H_2SO_4$ (19 c.c.) and 65% $SO_3$-$H_2SO_4$ (1 c.c.). The phosphine dissolved and the solution was heated on a water bath. The solution was tested at intervals by adding one drop to water (2–3 c.c.) until a test drop gave a clear or only slightly cloudy aqueous solution (1–2 hours depending on the acid strength). The acid solution was cooled, poured cautiously into water (200 c.c.) and neutralized with saturated sodium hydroxide solution. The product separated as fine, white shining leaves.

As demonstrated in comparative Example 3, the sodium m-diphenyl phosphino benzene sulfonate (i.e., $Ph_2P(m-C_6H_4SO_3Na)$) ligand which was synthesized by direct sulfonation of triphenyl phosphine resulted in very low rates of reaction in the hydroformylation of 1-decene and a low selectivity to the desired normal isomer compared to the corresponding para substituted carboxylic or sulfonic acid ligands.

Sodium p-diphenyl phosphino sulfonate, i.e., $Ph_2P(p-C_6H_4SO_3Na)$, was first synthesized by H. Schindlbauer (see H. Schindlbauer, *Monatsh Chem*, 96 (6), 1965, pp. 2051) from potassium diphenyl phosphide and p-chloro sodium benzoate by boiling at 67° C. in tetrahydrofuran (THF) for 24 hours. This article describes the formation of a by-product, p-diphenyl phosphino benzene, i.e., $Ph_2P(p-C_6H_4PPh_2)$, resulting from displacement of the sulfonic group by the diphenyl phosphino group, but gives no yield for the sulfonic salt, i.e., $Ph_2P(p-C_6H_4SO_3Na)$, which was identified by elemental analysis for phosphorus and sulfur but could not be recrystallized due to poor solubility The present inventors have discovered that by using a lithium salt of the p-chloro benzene sulfonic acid, i.e., $Cl(p-C_6H_4SO_3Li)$ in a reaction with potassium diphenyl phosphide enables the isolation and purification of the product compound in high yield and purity. Since the lithium salt is more soluble then the corresponding sodium salt in THF, the reaction proceeds in 0.5 hours in boiling THF which is substantially faster than the formation of $Ph_2P(pCC_6H_4SO_3Na)$ from $Cl(p-C_6H_4SO_3Na)$. Moreover, the potassium salt ($Ph_2P(p-C_6H_4SO_3K)$) of the ligand as a result of a lithium/potassium salt exchange is obtained in an approximate yield of 50%. Also, the potassium salt of the ligand was found to be less soluble in organic solvents then the conventional sodium salts, such that it was able to be recrystallized from EtOH. The potassium salt was identified by elemental analysis, IR and P31 NMR.

Conventional hydroformylation reactions take place in an aqueous emulsion, such as that described in Great Britain Application No. 2,085,874, filed Aug. 21, 1981, in which the aqueous phase consists of a 1N $NaHCO_3$ solution, thus generating an excess of sodium cations. Therefore, since the potassium ligand salt is soluble in water it is consequently exchanged "in situ" to the sodium salt. As such, when the $Ph_2P(p-C_6H_4SO_3K)$ ligand complexed catalyst is used to hydroformylate 1-decene it exhibits comparable rates of conversion to both $Ph_2P(p-C_6H_4SO_3Na)$ and $Ph_2P(p-C_6H_4COO_3Na)$ ligands, and substantially higher rates of conversion than $Ph_2P(m-C_6H_4SO_3Na)$.

The present invention also provides many additional advantages which shall become apparent as described below.

SUMMARY OF THE INVENTION

A method for producing a potassium para-diphenyl phosphino sulfonate ligand by reacting potassium diphenyl phosphide with a lithium salt of para-chloro benzenesulfonic acid in the presence of at least one compound selected from the group consisting of: tetrahydrofuran, 1,4-dioxane and 2-ethoxyethyl ether, at a temperature in the range between about 65° to about 100° C. for between about 0.25 to 1 hours.

This group VIII noble metal-ligand complex catalyst is preferably used in hydroformylation of olefins in the presence of synthesis gas. The present invention also encompasses a method for producing higher aldehydes and higher alcohols by hydroformylating an olefinic feedstock with synthesis gas in the presence of this novel Group VIII noble metal-ligand complex catalyst which forms a crude reaction product of an olefin feed, a hydroformylation reaction product and the Group VIII noble metal-ligand complex catalyst.

Other and further objects, advantages and features of the present invention will be understood by reference to the following specification.

DESCRIPTION OF THE PREFERRED EMBODIMENTS

Hydroformylation is a process of converting olefins to a product of one or more additional carbon numbers by the addition of carbon monoxide and hydrogen to the double bond(s) of the olefin in the presence of a catalyst at elevated temperatures and pressures. A typical hydroformylation process is demonstrated below:

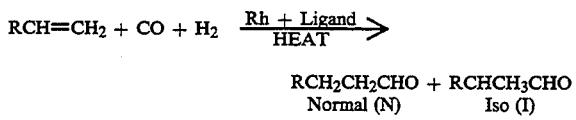

$$RCH=CH_2 + CO + H_2 \xrightarrow[HEAT]{Rh + Ligand}$$

$$\underset{\text{Normal (N)}}{RCH_2CH_2CHO} + \underset{\text{Iso (I)}}{RCHCH_3CHO}$$

At a temperature of 100° C. and a pressure of 12.75 kg (150 lbs.) the normal to iso ratio using rhodium as the catalyst may be below 1 or even as high as 100, depending on the ligand, ratio of ligand to rhodium, etc. Homogeneous rhodium-ligand complex catalysts are able to take a linear terminal olefin and convert it into a predominantly linear aldehyde.

A potassium para-diphenyl phosphino sulfonate ligand is formed by reacting potassium diphenyl phosphide with a lithium salt of para-chloro benzenesulfonic acid in the presence of at least one compound selected from the group consisting of: tetrahydrofuran, 1,4-dioxane and 2-ethoxyethyl ether, at a temperature in the range between about 65° to about 100° C. for between about 0.25 to 1 hours.

The potassium diphenyl phosphide is produced from the reaction product of diphenyl chloropnosphine and potassium in the presence of at least one compound selected from the group consisting of: tetrahydrofuran, 1,4-dioxane and 2-ethoxyethyl ether, at a temperature in the range between about 65° to about 100° C. for between about 0.25 to 1 hours.

The potassium para-diphenyl phosphino sulfonate ligand ($Ph_2P(p-C_6H_4SO_3K)$) according to the present invention is preferably synthesized from potassium diphenyl phosphide ($Ph_2PK$) and the lithium salt of p-chloro benzenesulfonic acid ($Cl(p-C_6H_4SO_3Li)$) by boiling in tetrahydrofuran (THF) for approximately 0.5 hours as shown in the below equations:

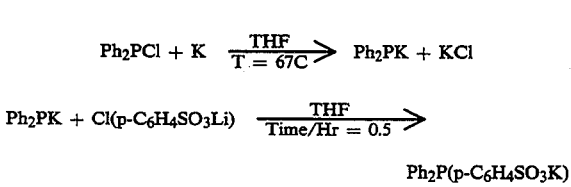

$$Ph_2PCl + K \xrightarrow[T = 67C]{THF} Ph_2PK + KCl$$

$$Ph_2PK + Cl(p-C_6H_4SO_3Li) \xrightarrow[Time/Hr = 0.5]{THF}$$

$$Ph_2P(p-C_6H_4SO_3K)$$

Due to Li/K salt exchange, the yield of potassium p-diphenyl phosphino sulfonate during the synthesis process is approximately 50%. The potassium ligand salt is soluble in water. The hydroformylation takes place in an aqueous emulsion in which the aqueous phase consists of a 1N $NaHCO_3$ solution, thus giving an excess of sodium cations. The potassium salt of the ligand is consequently exchanged "in situ" with the sodium salt. The aqueous phase contains sodium bicarbonate and a surfactant such as lauric acid in addition to the ligand-sodium salt.

This Group VIII metal-ligand complex catalyst is particularly useful in producing higher aldehydes and higher alcohols which comprises hydroformylating an olefinic feedstock with synthesis gas in the presence of the Group VIII noble metal-ligand complex catalyst to form a crude reaction product comprised of an olefin feed, a hydroformylation reaction product and the Group VIII noble metal-ligand complex catalyst.

In the below examples, the organic phase solution contains the olefin, e.g., 1-decene, the Rh catalyst precursor, a co-solvent such as i-PrOH and, as an internal standard for gas chromatographic (GC) analysis, a nonreactive compound such as hexadecane. The two solutions are introduced in an autoclave and pressurized to 10 psig at room temperature with a mixture of carbon monoxide to hydrogen of 1:1. The autoclave is heated at 80° C. while the pressure is maintained at 150 psig. The reaction is monitored by periodic GC analysis of samples taken from the organic phase.

EXAMPLE 1

(Synthesis of $Ph_2P(p-C_6H_4SO_3K)$)

28.30 grams of diphenyl chlorophosphine were added to 10 grams of a finely dispersed suspension of potassium, the suspension of potassium was obtained under vigorous stirring in 400 ml of THF at 67° C. in a nitrogen atmosphere, dropwise at a sufficient rate to maintain constant reflux without external heating. As the reaction proceeded, the potassium disappeared and $Ph_2PK$ appeared as an intense purple compound. After the diphenyl chlorophosphine had been completely added to the suspension of potassium, the solution was cooled to 45°–50° C. Thereafter, 25.47 grams of a well dried p-chloro lithium sulfonate was added to the $Ph_2PK$ under a nitrogen blanket. This solution was then heated to reflux with stirring. The change in color from purple to light brown, which took place within 0.5 hours, indicated the disappearance of the potassium diphenyl phosphide. The solution was cooled, while stirring, to room temperature, and 250 cc of water was added. The mixture was extracted times with 100 cc of ether. The aqueous solution was concentrated on the rotary evaporator at 50°–60° C. to approximately half the original volume. A white precipitate appeared. The solution was cooled, filtered, washed with cold ethanol and dried under nitrogen to give 25 grams of product and a yield of 49% of $Ph_2P(p-C_6H_4SO_3K)$.

The compound analysis for $Ph_2P(p-C_6H_4SO_3K)$ having a molecular weight of 380 calculated for C=56.84, H=3.69, P=8.16, O=12/63, K=10.26 and S=8.42% found: C=56.68, H=3.93, P=7.51, K=10.36, S=8.01%. P31 NMR detected one peak of -3.6396 ppm (with 85% $H_3PO_4$ ext. reference). The IR=1210-1050, CM- for $SO_3$-, 827 CM-1 1,4 disubst. benzene, 1479, 750,697 CM-1 for $(C_6H_5)_2P$.

The lithium p-chloro benzene sulfonate was obtained from the corresponding acid by exchange with LiOH in aqueous ethanol, neutralization of the excess LiOH with carbon dioxide, and drying ASTM/Toluene followed by high vacuum.

EXAMPLE 2

(Sodium p-Diphenyl Phosphino Benzoate Ligand)

2 grams of lauric acid, as surfactant, were added to an aqueous solution of which consisted of sodium p-diphenyl phosphino benzoate ($Ph_2P(p-C_6H_4COO_3Na)$), dissolved at approximately 70° C. with stirring under nitrogen in 70 grams of 1N $NaHCO_3$ solution. The resulting clear solution was then introduced through a Hoke bomb to a 1 liter autoclave. To this solution, a mixture which consisted of 179.23 gms of 1-decene, 9.93 grams of hexadecane as an internal standard, 1.24E-01 grams of rhodium acetate dimer (i.e., $RhII_2(OOCCH_3)_4$ dimer) and 10 grams of i-PrOH as cosolvent were introduced through the Hoke bomb under a carbon monoxide/hydrogen pressure.

The autoclave was pressurized with a mixture of $CO/H_2$ in a ratio of 1:1 and at a pressure of 100 psig at room temperature. The contents were then heated to 80° C. while the pressure was maintained at 150 psig. The reaction was monitored by periodic GC analysis of the organic layer. The data is set forth below in Table 1.

TABLE 1

| | | | Mole % | | | |
| Run No. | Ligand Type | Time Hour | Conversion of 1-Decene | Selectivity to Aldehyde | Ratio N/I | TON |
|---|---|---|---|---|---|---|
| 1 | $Ph_2P(p-C_6H_4SO_3Na)$ | 0.50 | 5.26 | 76.00 | 15.87 | 239 |
| 2 | $Ph_2P(p-C_6H_4SO_3Na)$ | 1.00 | 13.59 | 86.56 | 15.94 | 345 |
| 3 | $Ph_2P(p-C_6H_4SO_3Na)$ | 2.00 | 21.50 | 88.83 | 15.69 | 172 |
| 4 | $Ph_2P(p-C_6H_4SO_3Na)$ | 3.00 | 31.47 | 91.24 | 15.14 | 213 |
| 5 | $Ph_2P(p-C_6H_4SO_3Na)$ | 4.00 | 42.25 | 91.42 | 14.95 | 243 |

TON = Moles Conv. (Sel to Ald./100)/g.at. Rh Hr.

EXAMPLE 3

(Sodium m-Diphenyl Phosphino Benzene Sulfonate Ligand)

2 grams of lauric acid, as surfactant, were added to an aqueous solution of which consisted of sodium m-diphenyl phosphino benzene sulfonate ($Ph_2P(m-C_6H_4SO_3Na)$), dissolved at approximately 70° C. with stirring under nitrogen in 70 grams of 1N $NaHCO_3$ solution. The resulting clear solution was then introduced through a Hoke bomb to a 1 liter autoclave. To this solution, a mixture which consisted of 181.56 grams of 1-decene, 12.20 grams of hexadecane as an internal standard, 1.22E-01 grams of $RhII_2(OOCCH_3)_4$dimer and 1.0 grams of i-PrOH as co-solvent were introduced through the Hoke bomb under a carbon monoxide/hydrogen pressure.

The autoclave was pressurized with a mixture of $CO/H_2$ in a ratio of 1:1 and at a pressure of 100 psig at room temperature. The contents were then heated to 80° C. while the pressure was maintained at 150 psig. The reaction was monitored by periodic GC analysis of the organic layer. The data is set forth below in Table 2.

TABLE 2

| Run No. | Ligand Type | Time Hour | Mole % Conversion of 1-Decene | Mole % Selectivity to Aldehyde | Ratio N/I | TON |
| --- | --- | --- | --- | --- | --- | --- |
| 1 | $Ph_2P(m-C_6H_4SO_3Na)$ | 0.50 | 0.55 | 34.18 | 13.35 | 25 |
| 2 | $Ph_2P(m-C_6H_4SO_3Na)$ | 1.00 | 0.57 | 33.12 | 9.85 | 13 |
| 3 | $Ph_2P(m-C_6H_4SO_3Na)$ | 2.00 | 0.78 | 41.04 | 6.82 | 9 |
| 4 | $Ph_2P(m-C_6H_4SO_3Na)$ | 18.00 | 3.27 | 83.25 | 6.39 | 4 |

EXAMPLE 4

(Potassium p-Diphenyl Phosphino Benzene Sulfonate Ligand)

2 grams of lauric acid, as surfactant, were added to an aqueous solution of which consisted of sodium p-diphenyl phosphino benzene sulfonate ($Ph_2P(p-C_6H_4SO_3K)$), dissolved at approximately 70° C. with stirring under nitrogen in 70.84 grams of 1N $NaHCO_3$ solution. The resulting clear solution was then introduced through a Hoke bomb to a 1 liter autoclave. To this solution, a mixture which consisted of 180.13 grams of 1-decene, 10.34 grams of hexadecane as an internal standard, 1.44E-01 grams of rhodium carbonyl acetyl acetonate ($RhI(CO)_2(C_5H_7O_2)$) and 15 grams of i-PrOH as co-solvent were introduced through the Hoke bomb under a carbon monoxide/hydrogen pressure.

The autoclave was pressurized with a mixture of $CO/H_2$ in a ratio of 1:1 and at a pressure of 100 psig at room temperature. The contents were then heated to 80° C. while the pressure was maintained at 150 psig. The reaction was monitored by periodic GC analysis of the organic layer. The data is set forth below in Table 3.

TABLE 3

| Run No. | Ligand Type | Time Hour | Mole % Conversion of 1-Decene | Mole % Selectivity to Aldehyde | Ratio N/I | TON |
| --- | --- | --- | --- | --- | --- | --- |
| 1 | $Ph_2P(p-C_6H_4SO_3K)$ | 0.50 | 11.30 | 94.50 | 14.86 | 505 |
| 2 | $Ph_2P(p-C_6H_4SO_3K)$ | 1.00 | 16.62 | 94.52 | 13.56 | 238 |
| 3 | $Ph_2P(p-C_6H_4SO_3K)$ | 2.50 | 33.81 | 94.20 | 13.23 | 257 |
| 4 | $Ph_2P(p-C_6H_4SO_3K)$ | 4.00 | 49.00 | 94.47 | 13.06 | 225 |
| 5 | $Ph_2P(p-C_6H_4SO_3K)$ | 10.00 | 85.87 | 95.53 | 12.62 | 135 |

When Tables 1, 2 and 3 are compared it becomes abundantly clear that the rhodium hydroformylation of 1-decene with potassium p-diphenyl phosphine benzene sulfonate ($Ph_2P(p-C_6H_4SO_3K)$) exhibited slightly higher rates of conversion as compared to $Ph_2P(p-C_6H_4COO_3Na)$. For example, after 4 hours of reaction in the hydroformylation reactor the rhodium catalyst of the present invention having a $Ph_2P(p-C_6H_4SO_3K)$ ligand converted approximately 49.00 mole percent of 1-decene to aldhyde, whereas the conventional rhodium catalyst with a $Ph_2P(p-C_6H_4COO_3Na)$ ligand only converted approximately 42.25 mole percent. Furthermore, the $Ph_2P(p-C_6H_4SO_3K)$ converted more than twenty times as much as the rhodium catalyst with a $Ph_2P(m-C_6H_4SO_3Na)$ ligand. The rhodium catalyst with a $Ph_2P(p-C_6H_4SO_3K)$ ligand also exhibited an increased selectivity to aldehydes verses the $Ph_2P(p-C_6H_4COO_3Na)$ and $Ph_2P(m-C_6H_4SO_3Na)$ ligands.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

What is claimed is:

1. A method for producing higher aldehydes and higher alcohols which comprises hydroformylating an olefinic feedstock at elevated temperatures with synthesis gas in the presence of a Group VIII noble metal-ligand complex catalyst to form a crude reaction product comprised of an olefin feed, a hydroformylation reaction product and a Group VIII noble metal-ligand complex catalyst, wherein said Group VIII noble metal-ligand complex catalyst is a Group VIII noble metal complexed with a potassium para-diphenyl phosphino sulfonate ligand.

2. The method according to claim 1 wherein said potassium para-diphenyl phosphino sulfonate ligand is the reaction product of potassium diphenyl phosphide and a lithium salt of para-chloro benzenesulfonic acid.

3. The method according to claim 2 wherein said potassium diphenyl phosphide and lithium salt of para-chloro benzenesulfonic acid are reacted in the presence of at least one compound selected from the group consisting of: tetrahydrofuran, 1,4-dioxane and 2ethoxyethyl ether.

4. The method according to claim 2 wherein said potassium diphenyl phosphide and lithium salt of para-chloro benzenesulfonic acid are heated at a temperature in the range between about 65° to about 100° C.

5. The method according to claim 2 wherein said potassium diphenyl phosphide and lithium salt of para-chloro benzenesulfonic acid are reacted for between about 0.25 to about 100 hours.

6. The method according to claim 2 wherein said potassium diphenyl phosphide is produced from the reaction product of diphenyl chlorophosphine and potassium.

7. The method according to claim 6 wherein said diphenyl chlorophosphine and potassium are reacted in the presence of at least one compound selected from the group consisting of: tetrahydrofuran, 1,4-dioxane and 2-ethoxyethyl ether.

8. The method according to claim 6 wherein said diphenyl chlorophosphine and potassium are reacted at a temperature in the range between about 65° to about 100° C.

9. The method according to claim 1 wherein said olefinic feedstock is a $C_6$ to $C_{12}$ olefin.

10. The method according to claim 9 wherein said olefinic feedstock is 1-decene.

11. The method according to claim 1 wherein said olefinic feedstock is reacted with synthesis gas in the presence of a Group VIII noble metal-ligand complex catalyst at a temperature of about 80° C.

* * * * *